United States Patent

Modolo et al.

[11] Patent Number: 5,966,584
[45] Date of Patent: Oct. 12, 1999

[54] METHOD OF SEPARATING TRIVALENT ACTINIDES FROM TRIVALENT LANTHANIDES

[75] Inventors: Giuseppe Modolo, Jülich; Reinhard Odoj, Gey, both of Germany

[73] Assignee: Forschungszentrum Julich GmbH, Julich, Germany

[21] Appl. No.: 08/931,894

[22] Filed: Sep. 17, 1997

[51] Int. Cl.[6] .......................... C01G 56/00; B01D 11/00; C01F 17/00
[52] U.S. Cl. ..................... 423/7; 423/2; 423/7; 423/8; 423/9; 423/10; 423/20; 423/21.1; 423/21.5
[58] Field of Search ................................ 423/7, 9, 10, 8, 423/2, 20, 21.5, 21.1

[56] References Cited

U.S. PATENT DOCUMENTS

| | | | |
|---|---|---|---|
| 3,812,232 | 5/1974 | Bauer et al. | 423/21 |
| 3,993,728 | 11/1976 | Schulz | 423/9 |
| 4,021,313 | 5/1977 | Hausberger et al. | 204/1.5 |
| 4,461,747 | 7/1984 | Fitoussi et al. | 423/10 |
| 4,548,790 | 10/1985 | Horwitz et al. | 423/9 |
| 4,572,802 | 2/1986 | Hubert et al. | 534/12 |
| 4,574,072 | 3/1986 | Horwitz et al. | 423/9 |
| 4,867,951 | 9/1989 | Smith et al. | 423/9 |
| 5,256,383 | 10/1993 | Cordier et al. | 423/9 |
| 5,470,553 | 11/1995 | Hao-Chung et al. | 423/139 |
| 5,639,433 | 6/1997 | Yuan et al. | 423/21.5 |

OTHER PUBLICATIONS

Actinide–Lanthanide Group Separation Using Sulfur and Nitrogen Donor Extractants Claud Musikas, 12 pages.

"Chinese Experience in the Romoval of Actinides from Highly Active Waste . . . ", Yong Zhu, Institute of Nuclear Energy Technology, vol. 108, Dec. 94, 9 pages.

"Extraction of Reserpine and Other Alkaloids from Colombian *Rauwolfia hirsuta*", (Dept. of Experimental Therapeutics, Labor.Cup), Ww.A Higgins, 12 pages.

Selctive Extraction of Trivalent Actinides from Lanthuanides . . . , G.D.Jarvinca., Texas Tech University 1993, 8 pages.

"Extraction Separation of Trevalent Americium and Lanthanides . . . " J.Rais, Nuclear Research Institute, Czech Republic, Separation Science & Techno., 19(10)pp.1347–1365, 1994.

"A Cross–Flow Hot Test for Separating AM from Fission . . . " Jing Chen, Radiochimica Acta 76, 129–130 1997,2 pages.

"Partitioning Studies in China and the Separation of Americium . . . " Yongjun Zim, Inst.Nucl.Energy Tech.,4 pages.

"A Review of the Basic Chemistry and Recent Developments . . . " Kenneth L.Nash, Solvent extraction & Ion Exchange, 11(4),729–768 (1993).

"The Separation of AM from Lanthanides by Purified Cyanex 301 Extraction" Jing Chen, Sep.Science & Tech. 31 (19), pp. 2723–2731.

"The Synthesis and Actinide and Lanthanide Complexation of "Soft"Donor Lignads: . . . ", Barbara F. Smith, Sovent Extraction & Ion Exchange, 7(5), 749–765 (1989).

*Primary Examiner*—Gary P. Straub
*Assistant Examiner*—Cam N. Nguyen
*Attorney, Agent, or Firm*—Herbert Dubno

[57] ABSTRACT

Trivalent actinides can be separated from trivalent lanthanides in aqueous solutions at $H^+$ concentrations of 2 mol/l to 0.001 mol/liter by extraction with bis(aryl) dithiophosphinic acid and a synergist such as TBP, TOPO and TBPO in an organic solvent. A high separation efficiency results. The method is applicable to high-level liquid waste from reactors and nuclear-material processing plants.

12 Claims, 8 Drawing Sheets

Extraction of trace amounts of Am(III) and Eu (III) with 0.5 M dithiophosphinic acid and 0.25 M TBP in toluene from $HNO_3$.

FIG.1

Extraction of trace amounts of Am(III) and Eu (III) with 0.5 M dithiophosphinic acid and 0.25 M TBP in toluene from $HNO_3$.

FIG. 2

Extraction of trace amounts of Am (III) and Eu (III) with bis(chlorophenyl) dithiophosphinic acid from 0.2 $\underline{M}$ HNO for $(Cl-C_6H_5)_2PS(SH)$ variation the TBP concentration was 0.25 $\underline{M}$ for TBP variation the $(Cl-C_6H_5)_2PS(SH)$ conection was 0.5 $\underline{M}$.

FIG. 3

Extraction of trace amounts of Am (III) and Eu (III) with 0.5 M bis(chlorophenyl)-dithiophosphinic acid and 0.25 M tri-n-octyl-(TOPO) or tri-n butyl phosphine oxide (TBPO) in toluene from HNO . The comparison with 0.25 M TOPO in toluene.

FIG.4

TOPO dependency for Am(III) and Eu(III) extraction with 0.5 M bis(chlorophenyl)dithiophosphinic acid in toluene from 0.4 M $HNO_3$.

FIG.5

Extraction of trace amounts of Am(III) and Eu (III) with 0.5 M dithiophosphinic acid and 0.5 M TBP in toluene from HNO
The comparison of $(C_6H_5)_2PS(SH)$ with $(CH_3-C_6H_4)_2PS(SH)$

FIG. 6

Extraction of trace amounts of Am(III) and Eu(III) with Bisphenyldithiophiophosphinic acid from 0.55 M HNO For $(C_6H_5)_2PS(SH)$ variation the TBP concentration was 0.25 M For TBP variation the $(C_6H_5)_2PS(SH)$ concentration was 0.5 M

FIG. 7

Extraction of trace amounts of Am(III) and Eu (III) with 0.5 M Bispherryldithiophosphimic acid and 0.25 M TBP in toluene from $HNO_3$. The initial aqueousphase was a solution of < $10^{-7} M\ ^{241}Am, ^{152}Eu$ and 0.001 M La,Y,Ce,Pr,Nd,Sm,Eu,Gd in $HNO_3$.

FIG.8

Extraction of trace amounts of Am(III) and Eu (III) with 0.5 M Bis(chlorophenyl)dithiophosphinic acid and 0.25 M TBP in toluene from $HNO_3$. The initial aqueous phase was a solution of $<10^{-7}$ M $^{241}$Am, $^{152}$Eu and 0.001 M La, Y, Ce, Pr, Nd, Sm, Eu, Gd in $HNO_3$

METHOD OF SEPARATING TRIVALENT ACTINIDES FROM TRIVALENT LANTHANIDES

FIELD OF THE INVENTION

Our present invention relates to the separation of trivalent actinides from trivalent lanthanides in aqueous acidic solutions, especially radioactive waste solutions and, more particularly, to an extraction process involving the selective extraction of trivalent actinides from such solutions.

BACKGROUND OF THE INVENTION

It has been recognized that the hazard potential of radioactive waste can be reduced by separating the long-lived uranium and transuranium elements, hereinafter referred to as actinides, and their subsequent transmutation into short-lived or even stable nuclides. Specific attention has been directed in this regard to so-called high-level liquid wastes (HLLW) which contain, in addition to the actinides, sufficient quantities of lanthanides, i.e. elements ranging in atomic number from 58 to 71, which can effect efficiency of transmutation because of the high neutron absorption cross sections of lanthanides.

Chemical separation of trivalent actinides (An) from lanthanides (Ln) is a difficult separation because of the great chemical and physical similarity of the elements of the two groups and because of the similar ionic radii of the metals and their oxidation characteristics.

Hence efforts have been made to accomplish this separation by extraction techniques. For example, a commercial product known as Cyanex 301 has been identified as capable of yielding a very high Am (III)/Eu(III) separation factor. The key ingredient of the Cyanex 301 for extraction purposes, i.e. the key component of the extractant, is bis(2, 2,4 trimethylpentyl)-dithiophosphinic acid.

The extraction practice in earlier techniques of this type at a pH above about 3 which has not been convenient to highly acidic wastes for which such extractions are of the greatest importance.

By and large, therefore, earlier systems for the selective extraction of trivalent lanthanides from acidic aqueous solutions including high-level liquid wastes have not been fully satisfactory. Mention may also be made of the hydrometallurgical technique for separating lower atomic number metals described in U.S. Pat. No. 4,721,605 and using dialkyldithrophosphinic acids.

OBJECTS OF THE INVENTION

It is, therefore, the principal object of the present invention to provide an improved method of separating trivalent lanthanides from trivalent actinides or vice versa in acidic aqueous solution, whereby the separation efficiency can be improved and the process can be effective with high-level liquid wastes such as those resulting from nuclear reactor operations and in processing plants for processing nuclear reactor products.

Another object of this invention is to overcome drawbacks of earlier extraction processes.

SUMMARY OF THE INVENTION

We have discovered that these objects can be obtained and a separation efficiency between trivalent actinides and trivalent lanthanides significantly improved when operations are carried out at $H^+$ concentrations of 2 mol/l to 0.001 mol/l utilizing as the principal extractant and the predominant extractant in the extraction solution, at least one bis(aryl) dithiophosphinic acid. We have found that the bis(aryl) dithiophosphinic acids allow operation ,i.e. extraction of trivalent actinides, from such highly acidic solutions at hydrogen ion concentrations which do not additionally require stabilization because of the high acid stability of the bis(aryl)dithiophosphinic acids, the latter being far more stable than the bis(2,2,4 trimethylpentyl)dithiophosphinic acid which has been used heretofore.

More particularly, the method of separating at least trivalent actinide elements from at least one trivalent lathanide element in aqueous acidic solutions can comprise the steps of:

(a) maintaining an $H^+$ concentration of the solution of substantially 2 mol/l to 0.001. mol/l; and (b) extracting the solution at the $H^+$ concentration of 2 mol/l to 0.001 mol/l with an extractant which consists at least predominantly of a bis(aryl)dithiophosphinic acid to selectively extract the trivalent actinide element from the solution.

Preferably the bis(aryl)dithiophosphinic acid has the formula $(R)_2PS(SH)$, where R is phenyl, naphthyl, halo-substituted phenyl or $C_1$ to $C_{12}$ straight or branched chain alkyl substituted phenyl, cyano-phenyl or nitrophenyl or naphthyl. The substitutents can be in any position and, where halophenyl is used, preferably a monohalo derivative with the substituent in the 4 position is employed.

The bis(aryl)dithiophosphinic acid can be selected from the group which consists of the dithiophosphinic acid selected from the group which consists of bis(phenyl) dithiophosphinic acid, bis(chlorophenyl)dithiophosphinic acid, bis(fluorophenyl)dithiophosphinic acid, and bis (methylphenyl) dithiophosphinic acid We have found that the extraction solution, which utilizes an aromatic compound, should contain an effective amount of at least an extraction synergist which consists of at least one extraction synergist formula:

where R' is $C_1$–$C_{18}$ alkyl or alkoxy, preferred extraction synergists are selected from the group which consists of tributylphosphate, tributylphosphine oxide, trioctylphosphine oxide and tris(2-ethylhexyl)phosphate.

The bis(aryl)dithiophosphinic acid can be present in a concentration of substantially 0.05 to 1.5M, preferably 0.1 to 0.8M while the extraction synergist is present in a concentration of 0.01 to 1M, preferably a concentration of 0.1 to 0.5M.

The solvent is preferably toluene, orthoxylene, paraxylene or mesitylene.

The bis(phenyl)dithiophosphinic acid was prepared by the procedures reported by W. A. Higgins, et al, Journal of the American Chemical Society, 771864–1866 (1955) and the P-chloro and P-fluorophenyl analog, which are prepared similarly. the yields were between 50 and 70% and the solid compounds were recrystallized from isopropanol to a purity greater than 99.5%.

The radiolytic stability of bis(chlorophenyl) and bis (phenyl)dithiophosphinic acid was tested by gamma irradiation in the cooling pond of the DIDO research reactor at the Research Centre Jülich. The gamma dose rate was approx. 4000 Gy/h. For the $^{31}$p-NMR investigations approximately 100 mg of solid dithiophosphinic acid was irradiated with a total dose of $4 \times 10^4$, $1 \times 10^5$, $5 \times 10^5$ and 1 c $10^6$ Gy.

Described below are extraction experiments in accordance with the invention in which Am(III) and Eu(III) are utilized as examples of the trivalent actinide and trivalent lanthanide, respectively. TOPO is trioctylphosphene oxide and, in our experience, tributylphosphene oxide TBPO can be used as a substitute for the TOPO or in addition to it.

The synergist ligands tributylphosphate (Aldrich, p.a. quality) TBP, TOPO (Merck, p.a. quality) were used as received without further purification. Variable concentrations of aromatic dithiophosphinic acids and synergist were dissolved in toluene (Burdick & Jackson, distilled in glass) as the diluent. The radiotracers ($<10^{-7}$ mol/l) $^{152}$Eu(III) and $^{241}$Am(III) (Blaseg Isotopendienst) were added from a stock solution simultaneously to the aqueous phase, which consists only of $HNO_3$ (0.01–1.5 mol/l). Equal volumes (2 ml) of phases were contacted for ten minutes at room temperature (21°C.). After centrifuging, an aliquot of 1 ml was sampled from both phases for analyses using a high-purity germanium spectrometer system (EG&G Ortec). The distribution ratio D was obtained as a ratio of the count rates in the organic phase in that in the aqueous phase.

The following extraction mechanism is proposed for the extraction of Am(III) and Eu(III) with dithiophosphinic acid (HA).

$$M^{3+} + 2(HA)_{2org} \leftrightarrow MA_3(HA)_{org} + 3H^+ \qquad (1)$$

M=Am,Eu

It can be seen from equation (1) that the extraction equilibrium also depends on acid strength. An (III)Ln(III) separation at low pH will be more effective with more acidic aromatic dithiophosphinic acids. The $pK_a$ values of bisphenyldiphosnic acids ($pK_a$=2.70+0.2) and bis(fluorophenyl)-dithiophosphinic acid ($pK_a$=2.62+0.4) determined by potentiometric titration are lower than that of Cyanex 301 ($pK_a$=2.87+0.3). This can be explained by the –M effect of the benzene ring.

When $(C_6H_5)_2PS(SH)$ was used alone, surprisingly, no extraction of Am(III) and Eu(III)(($D_{am,Eu}$<$10^{-4}$) from 1M $NaNO_3$ took place at an equilibrium pH of 1.6. After adding TBP, on the other hand, a selective extraction of Am(III) from $HNO_3$ acid solutions took place.

BRIEF DESCRIPTION OF THE DRAWING

The above and other objects, features, and advantages will become more readily apparent from the following description, reference being made to the accompanying drawing in which.

SPECIFIC DESCRIPTION

The various extraction results of the invention are detailed in the drawing for a variety of the dithiophosphinic acids with various synergists.

Figure 1:
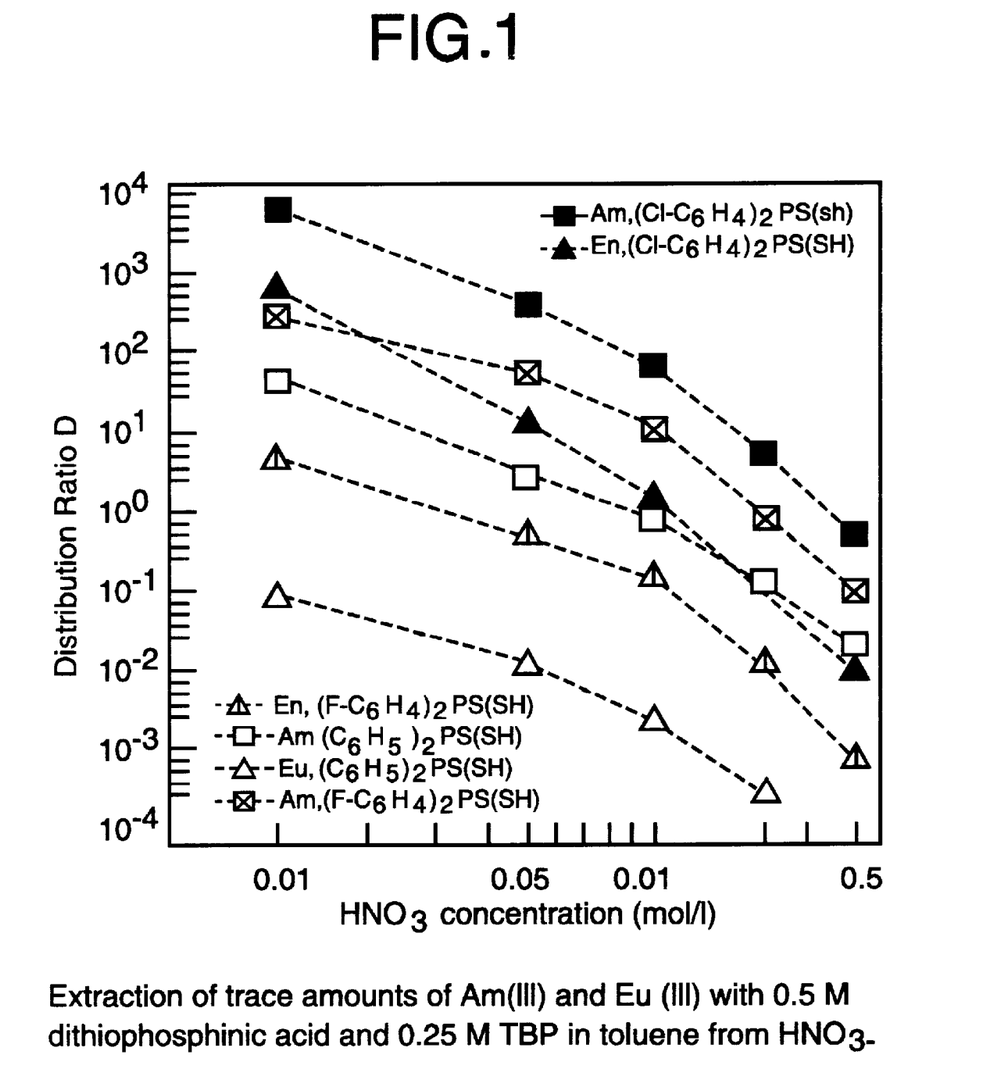
FIG. 1 is an extraction graph of trace amounts of Am(III) and Eu(III) with 0.5M dithiophosphinic acid and 0.25M TBP in toluene from $HNO_3$.

The extraction results with bisphenyldithiophosphinic acid, bis(chlorophenyl)dithiophosphinic acid, and bis (fluorophenyl)dithiophosphinic acid using TBP as the synergist from 0.01 to 0.4 mol/l nitric acid are shown in FIG. 1.

It can be seen that the extraction ratios of Am(III), Eu(III) strongly increase in the order $(C_6H_4)_2PS(SH) < F-C_6H_4)_2PS(SH) < (Cl-C_6H_4)_2PS(SH)$. However, the selectivity in the investigated acidity range decreases in the same order with Am/Eu separation factors of 230–280, 41–57 and 28–31. This suggests that the extraction can be improved by incorporating even stronger electron-attracting groups (such as $NO_2$ or two Cl groups), whereas selectivity inversely decreases. Of course, this also has an adverse effect on reextraction (stripping), which is then only possible with strongly acid $HNO_3$ (>1M).

Figure 2:
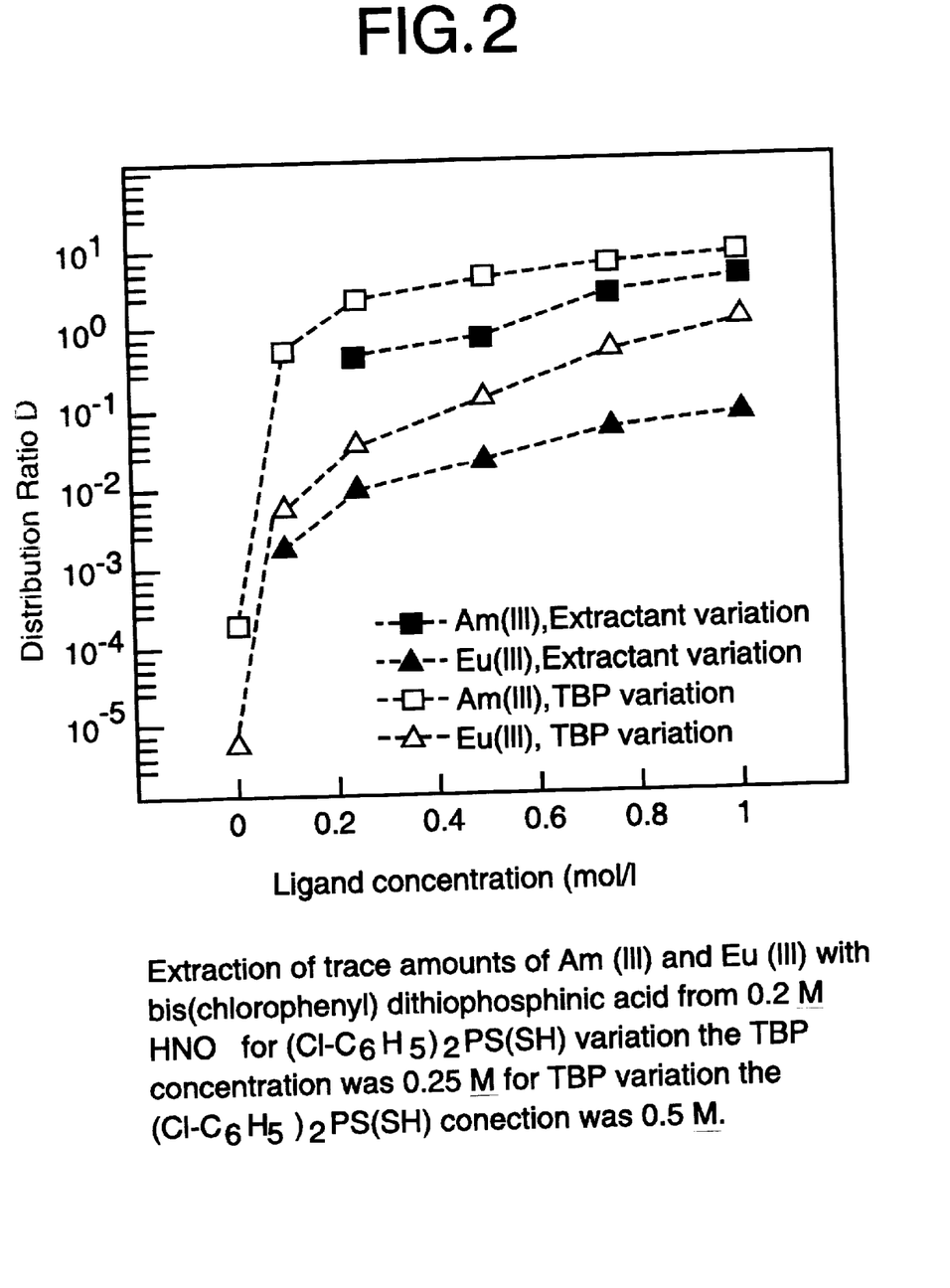
FIG. 2 is a graph showing the extraction of trace amounts of Am(III) and Eu(III) with bis(chlorophenyl)dithiophosphinic acid from 0.2M $HNO_3$. For $(Cl-C_6H_5)_2PS(SH)$ variation the TBP concentration was 0.25M. For TBP variation the $(Cl-C_6H_5)_2PS(SH)$ concentration was 0.5M.

The influence of the TBP concentration and of the extractant concentration during the extraction of Am(III) and Eu(III) with bis(chlorophenyl)dithiophosphinic acid from 0.2M $HNO_3$ is shown in FIG. 2. It can be seen that the Am(III) distribution ratio only continues to increase slightly at extractant concentrations >0.5M. The optimum TBP concentration ranges between 0.1 and 0.25M, where Am/Eu separation factors between 90 and 31 are achieved. No extraction is observed without TBP.

We furthermore investigated the synergistic effect with various neutral triorganylphosphates and phosphine oxides. Using mixtures of 0.25M trimethyl or triphenylphosphate and 0.5M bis(chlorophenyl)dithiophosphinic acid as the extractant, for example, no extraction of Am(III) and Eu(III) ($D_{am,Eu}$<$10^{-3}$) from 0.2M $HNO_3$ was observed. On the other hand, we observed a selective extraction of Am(III) with a distribution ratio $D_{am}$ of 2 and a high Am/Eu separation factor of >1000 under the same conditions using tris (2ethylhexyl)phosphate as the synergist. Obviously, the selectivity is caused by stearic hindrance. At the phase boundary, however, a white voluminous precipitate was observed, which made phase separation difficult and was presumably caused by co-extracted $HNO_3$ or $H_2O$. Therefore, no further investigations were carried out.

Figure 3:
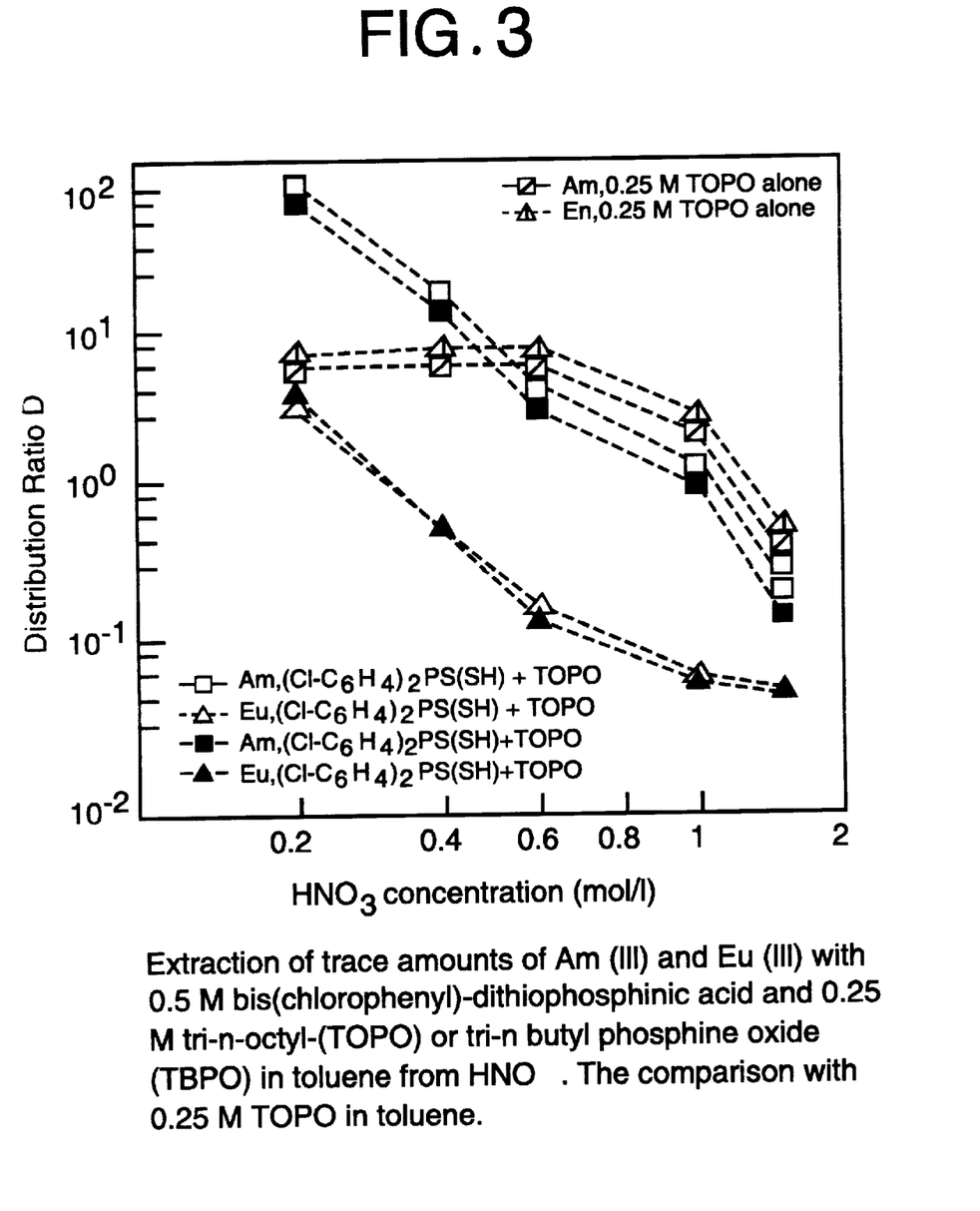
FIG. 3 is a graph showing the extraction of trace amounts of Am(III) and Eu(III) with 0.5M bis(chlorophenyl)-dithiophosphinic acid and 0.25 N tri-n-octyl- (TOPO) or tri-n-butyl phosphine oxide (TBPO) in toluene from $HNO_3$. The comparison with 0.25M TOPO in toluene.

The best results so far have been achieved with the synergistic combination of bis(chlorophenyl) dithiophosphinic acid and trioctylphosphine oxide (TOPO). Similar results were obtained with tributylphosphine oxide (TBPO). As can be seen from FIG. 3, the Am(III) distribution ratios increase by approximately two orders of magnitude compared to TBP (e.g. $D_{am,TOPO}$=152 and $D_{am,TBP}$=2, respectively, for 0.2M $HNO_3$) with comparable Am/Eu separation factors of approx. 30. The synergistic effect becomes even more apparent (FIG. 3) when comparing the extraction of Am(III) and Eu(III) using only TOPO, a typical hard donor extractant, which cannot discriminate between Am(III) and Eu(III). At acid concentrations <0.6 mol/l $HNO_3$ $D_{am(mixture)}$ increases and $D_{Eu(mixture)}$ decreases in comparison to $D_{am,Eu(TOPO\ alone)}$. On the other hand, it was observed for acid concentrations >0.6 mol/l that the Am(III) distribution ratio is comparable ($D_{am(mixture)} = D_{am,Eu(TOPO\ alone)}$) and that of Eu(III) $D_{Eu(mixture)} < D_{Eu(TOPO\ alone)}$) clearly decreases so that a separation takes place.

Figure 4:
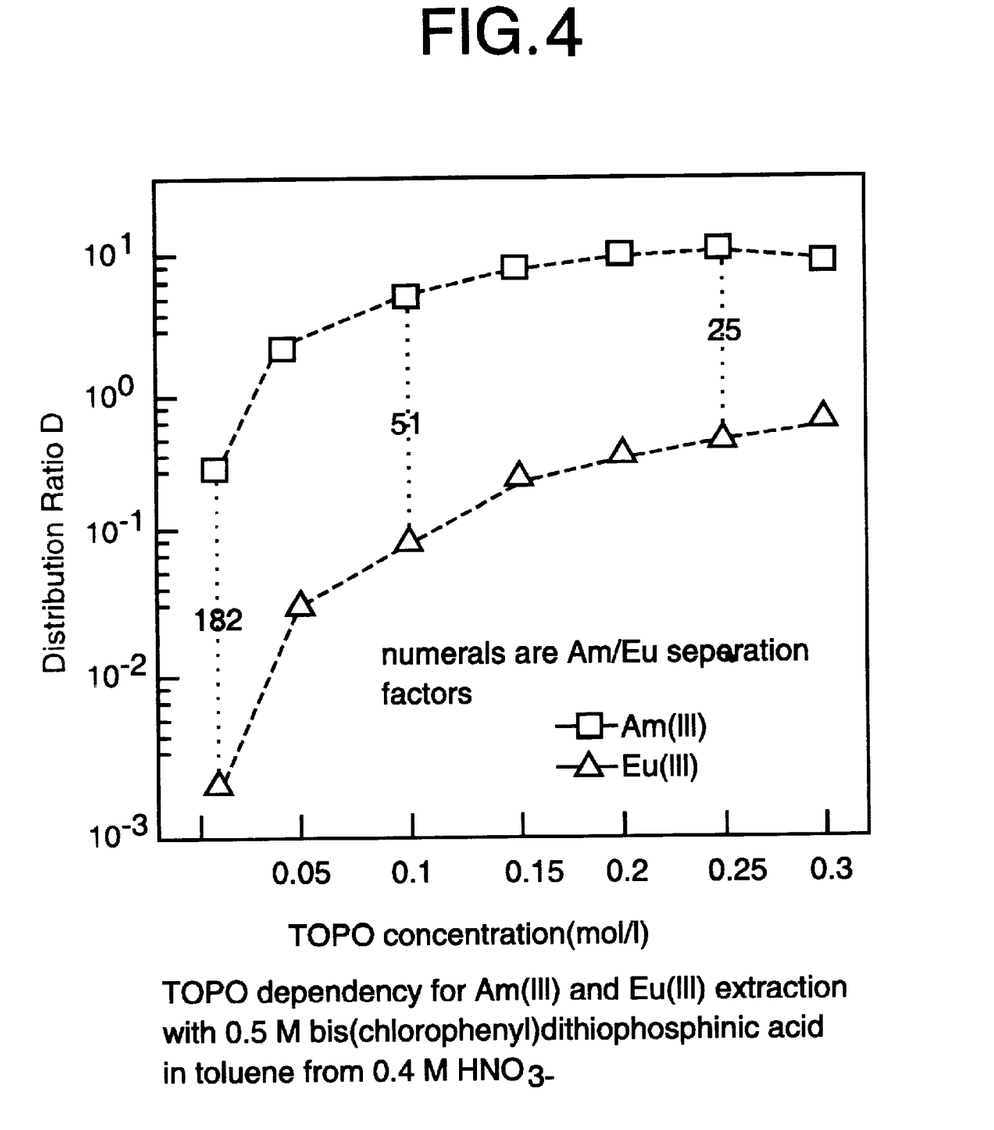
FIG. 4 is a graph showing the TOPO dependency for Am(III) and Eu(III) extraction with 0.5M bis(chlorophenyl)-dithiophosphinic acid in toluene from 0.4M $HNO_3$.

As can be seen from FIG. 4, the Am/Eu separation factors increase with decreasing TOPO concentrations. However, as in the case of using tris(2ethylhexyl)phosphate as the synergist, a precipitate was formed at TOPO concentrations <0.2 mol/l. This problem may perhaps be solved by using another solvent or adding a modifier, such as TBP.

An important aspect for partitioning is the irradiation behavior of the extractant. The extent of the radiolytic degradation of bisphenyl- and bis(chlorophenyl) dithiophosphinic acid was first determined by estimating the residual extractant content using quantitative $^{31}P$-NMR. Only slight decomposition (<2%) was observed after a high gamma dose of $1 \times 10^6$ Gy. This shows that the aromatic dithiophosphinic acids are clearly more stable than the dialkyl compound Cyanex 301. At the same dose of $1 \times 10^6$ Gy more than 80% of the Cyanex 301 had decomposed, forming approximately 6.3% Cyanex 302 (monothioderivate), 5% Cyanex 272 and a balance of undefinable compounds.

Figure 5:
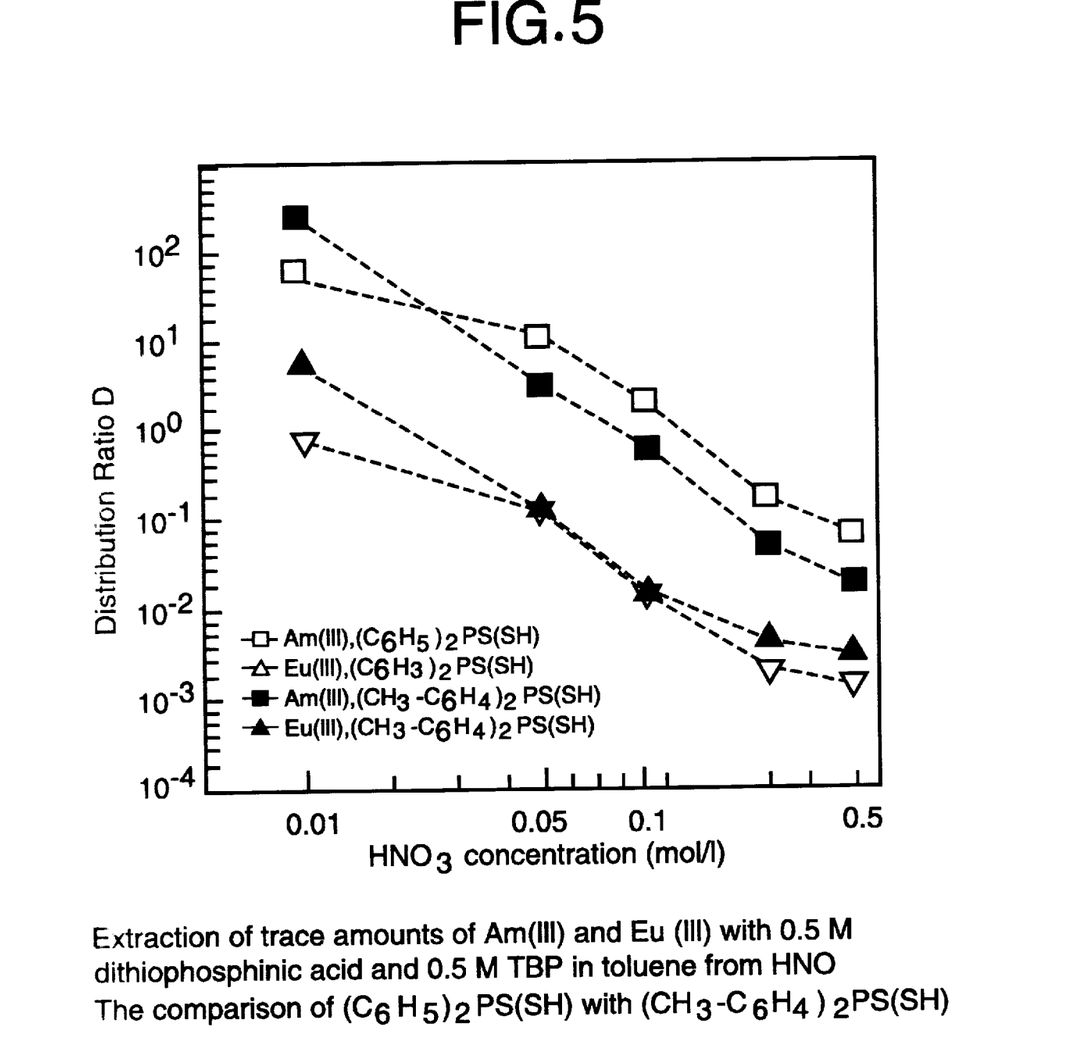
FIG. 5 is a graph showing the extraction utilizing extractants according to the invention with TBP as the synergist.

The extraction results with bisphenyl- and bis (methylphenyl)-dithiophosphinic acid are shown in FIG. 5. In the acidity range examined, the Am(III)/Eu(III) separation factors for $(C_6H_5)_2PS(SH)$ are 80 and thus significantly higher than for $(CH_3-C_6H_4)_2PS(SH)$ where they amount to approximately 15–40.

Figure 6:
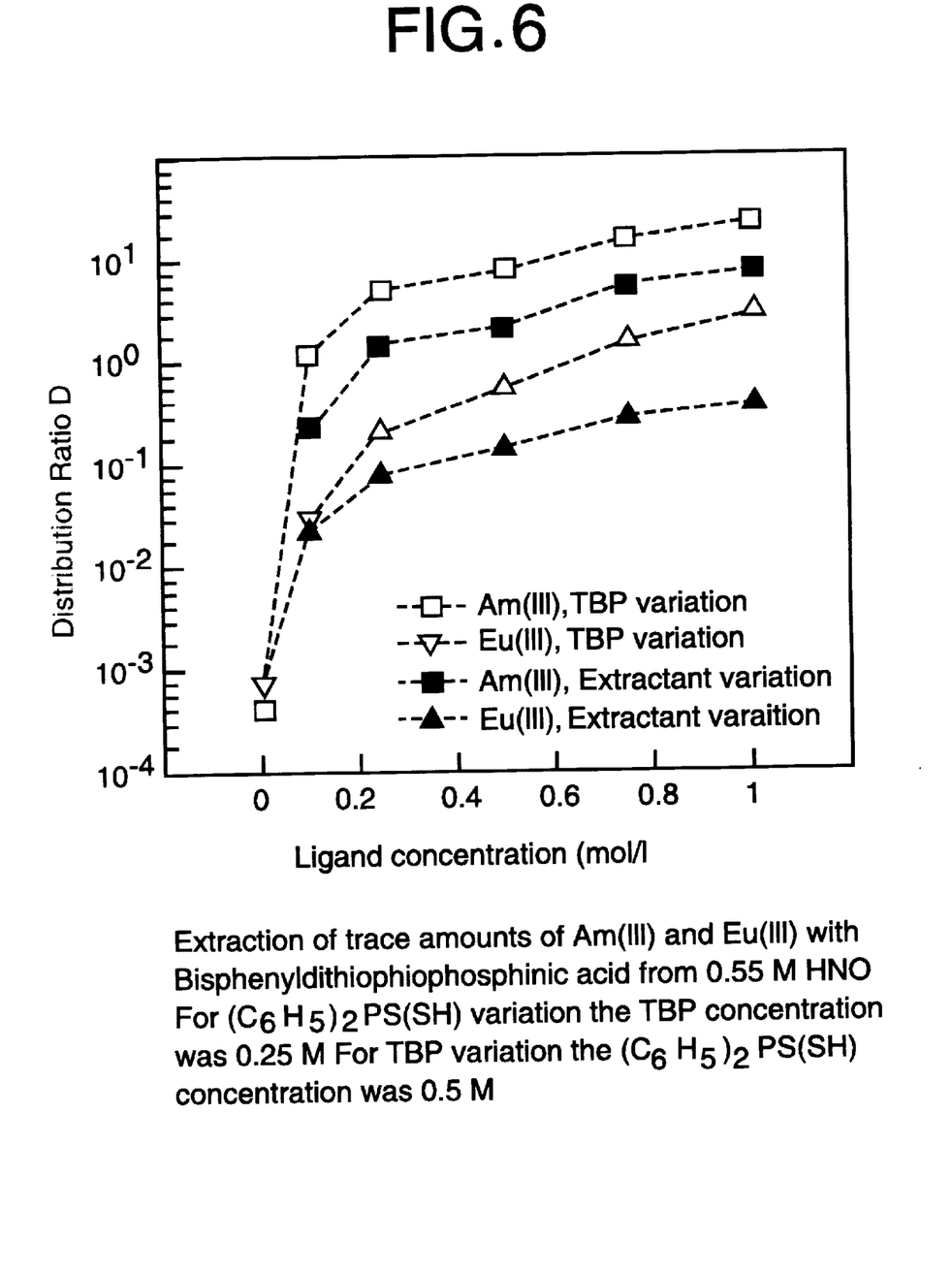
FIG. 6 is a graph of the distribution ratio versus ligand concentration with both variations in the synergist and in the extractant.

The influence of the TBP concentration and of the extractant concentration during the extraction of Am(III) and Eu(III) with bisphenyldithiophosphinic acid from 0.05M $HNO_3$ is shown in FIG. 6. It can be seen that the Am(III) distribution ratio only continues to increase slightly at extractant concentrations >0.5M. The optimum TBP concentration ranges between 0.1 and 0.25M, where Am/Eu separation factors between 460 and 290 are achieved. No extraction or separation is observed without TBP.

Figure 7:
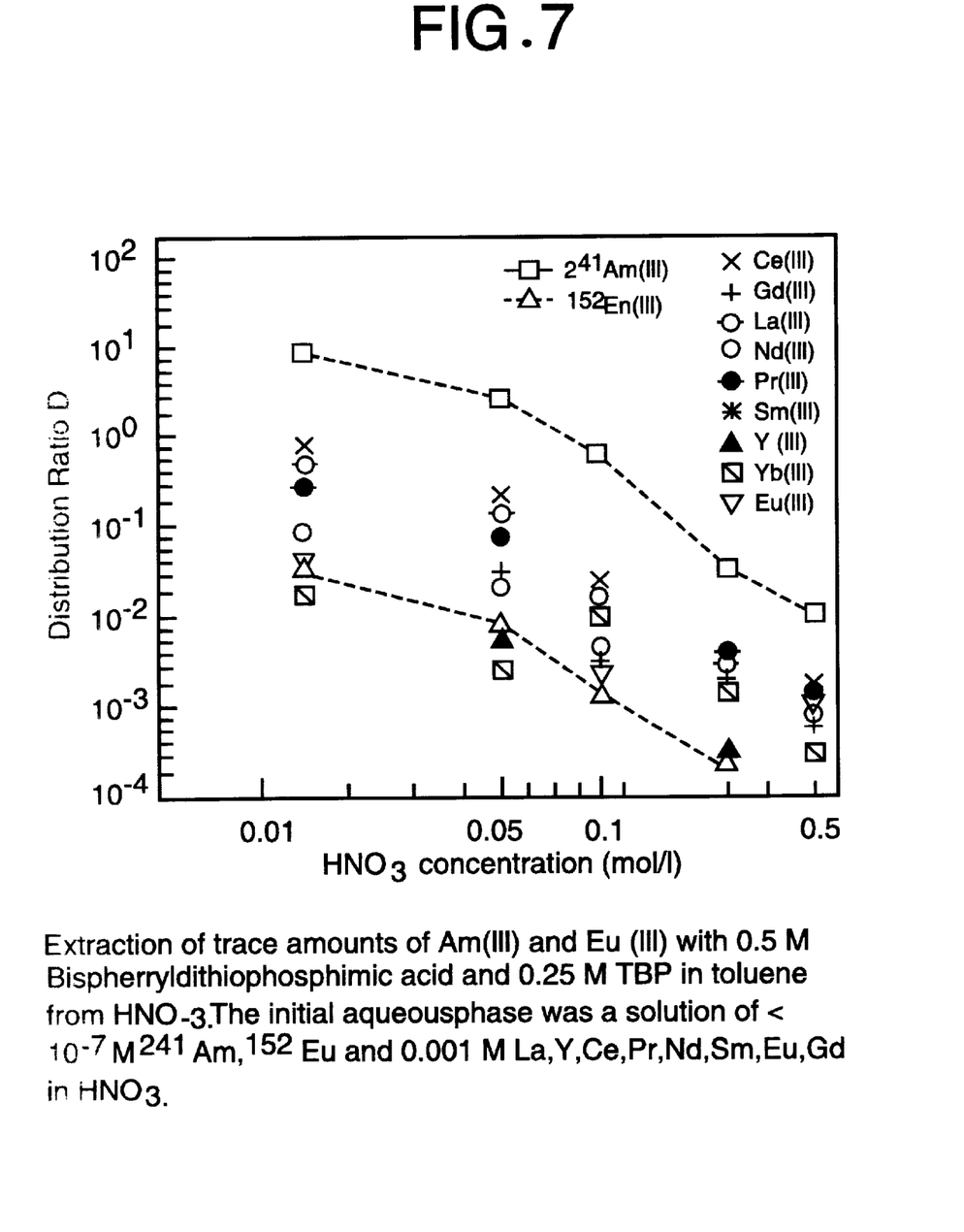
FIG. 7 is a graph showing extractions of Am(III), Eu(III) and lanthanides (III) from a solution containing traces of a large number of lanthanides.
Figure 8:
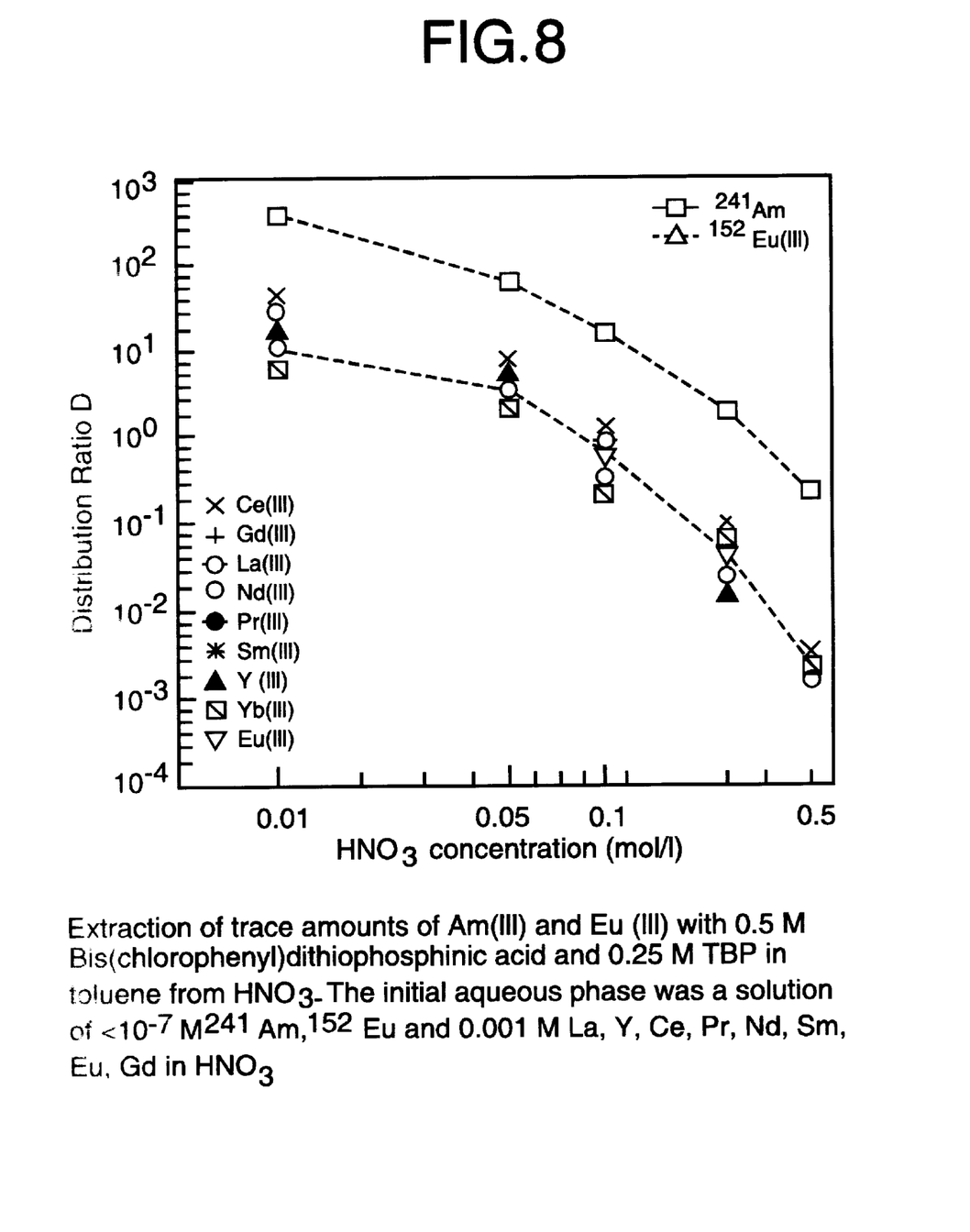
FIG. 8 is another extraction graph showing extraction in the presence of a large number of lanthanides.

In the presence of other lanthanides (FIG. 7), no influence on the extraction of Am(III) and Eu(III) can be observed. It can be seen, however, that e.g. Ce(III), La(III) and Pr(III) are clearly better extracted than Eu(III). Nevertheless, the Am(III)-lanthanide separation factors are between 40 and 1000 under the conditions specified in FIG. 7 (FIG. 8).

The results described were duplicated effectively with high level liquid wastes containing corresponding quantities of alanthanides and actinides.

While the invention has been described primarily with reference to $HNO_3$ systems, HCl and $H_2SO_4$ systems and mixed-acid systems are equally applicable.

We claim:

1. A method of separating at least one trivalent actinide element from at least one trivalent lanthanide element in an aqueous acidic solution containing said elements, said method comprising the steps of:
    (a) maintaining a $H^+$ concentration of said solution in a range of substantially 2 mol/l to 0.001 mol/l; and
    (b) extracting said solution at said $H^+$ concentration of 2 mol/l to 0.001 mol/l with an extractant which consists essentially of:
        (1) a bis(aryl)dithiophosphinic acid; and
        (2) at least one extraction synergist of the formula wherein R' is $C_1$ to $C_{18}$ alkyl or alkoxy, to selectively extract said trivalent actinide element from said solution.

2. The method defined in claim 1 wherein said bis(aryl) dithiophosphinic acid has the formula $(R)_2PS(SH)$, where R is phenyl, naphthyl, halo-substituted phenyl or naphthyl, alkyl-substituted phenyl or naphthyl where the alkyl group has 1 to 12 carbon atoms and is straight or branched chain, cyano-substituted phenyl or naphthyl or nitro-substituted phenyl or naphthyl.

3. The method defined in claim 1 wherein said bis(aryl) dithiophosphinic acid has the formula $(R)_2PS(SH)$, where R is phenyl, naphthyl, halo-substituted phenyl, alkyl-substituted phenyl where the alkyl group has 1 to 12 carbon atoms and is straight or branched chain, cyano-substituted phenyl or nitro-substituted phenyl.

4. The method defined in claim 3 wherein said bis(aryl) dithiophosphinic acid is selected from the group which consists of:
    bis(phenyl)dithiophosphinic acid,
    bis(chlorophenyl)dithiophosphinic acid,
    bis(fluorophenyl)dithiophosphinic acid and
    bis(methylphenyl)dithiophosphinic acid.

5. The method defined in claim 1 wherein said extraction synergist is selected from the group which consists of tributylphosphate, tributylphosphine oxide, trioctylphosphine oxide and tris(2-ethylhexyl)phosphate.

6. The method defined in claim 1 wherein said extraction synergist is a trialkylphosphine oxide.

7. The method defined in claim 1 wherein said aqueous acidic solution is a high-level liquid waste from a nuclear reactor or processing plant for nuclear materials.

8. The method defined in claim 1 wherein said extractant contains said bis(aryl)dithiophosphinic acid and said extraction synergist dissolved in an organic solvent.

9. The method defined in claim 8 wherein said organic solvent is selected from the group which consists of mesitylene, orthoxylene, paraxylene and toluene, and mixtures thereof.

10. The method defined in claim 1 wherein said aqueous acidic solution is a solution containing an acid selected from the group which consists of nitric acid, hydrochloric acid and sulfuric acid.

11. The method defined in claim 8 wherein said bis(aryl) dithiophosphinic acid is present in a concentration of substantially 0.05 to 1.5 M and said extraction synergist is present in a concentration of 0.01 to 1 M.

12. The method defined in claim 11 wherein said bis(aryl) dithiophosphinic acid is present in a concentration of substantially 0.1 to 0.8 M and said extraction synergist is present in a concentration of 0.1 to 0.5 M.

* * * * *